United States Patent
Araujo et al.

(10) Patent No.: US 8,715,631 B2
(45) Date of Patent: May 6, 2014

(54) COSMETIC MICROEMULSION

(75) Inventors: Karla Macian Araujo, São Paulo (BR); Jean-Luc Gezstesi, São Paulo (BR)

(73) Assignee: Natura Cosmetics S.A., Sao Paulo-SP (BR)

( * ) Notice: Subject to any disclaimer, the term of this patent is extended or adjusted under 35 U.S.C. 154(b) by 887 days.

(21) Appl. No.: 10/569,433

(22) PCT Filed: Aug. 27, 2004

(86) PCT No.: PCT/BR2004/000160
§ 371 (c)(1),
(2), (4) Date: Nov. 29, 2006

(87) PCT Pub. No.: WO2005/020938
PCT Pub. Date: Mar. 10, 2005

(65) Prior Publication Data
US 2007/0166265 A1    Jul. 19, 2007

(30) Foreign Application Priority Data
Aug. 29, 2003  (BR) ...................................... 0303286

(51) Int. Cl.
*A61K 8/60* (2006.01)
*A61K 8/06* (2006.01)
*A61Q 5/02* (2006.01)

(52) U.S. Cl.
CPC . *A61Q 5/02* (2013.01); *A61K 8/068* (2013.01); *A61K 8/604* (2013.01)
USPC ...................................... 424/70.13; 424/70.1

(58) Field of Classification Search
None
See application file for complete search history.

(56) References Cited

U.S. PATENT DOCUMENTS

| 5,646,100 A | * | 7/1997 | Haugk et al. .................. 510/131 |
| 5,656,278 A | * | 8/1997 | Enjolras ........................ 424/401 |
| 5,756,079 A | | 5/1998 | Cauwet et al. |
| 5,876,702 A | * | 3/1999 | Gers-Barlag et al. ........... 424/59 |
| 5,968,495 A | * | 10/1999 | Bolich et al. ............... 424/70.12 |
| 5,980,874 A | | 11/1999 | Foerster et al. |
| 6,013,270 A | * | 1/2000 | Hargraves et al. ............. 424/401 |
| 6,315,989 B1 | | 11/2001 | Narasimhan et al. |
| 6,488,946 B1 | * | 12/2002 | Milius et al. .................. 424/401 |
| 6,555,119 B1 | | 4/2003 | Mori et al. |
| 6,635,702 B1 | * | 10/2003 | Schmucker-Castner et al. .............................. 524/291 |
| 6,902,737 B2 | * | 6/2005 | Quemin ........................ 424/401 |
| 2003/0181347 A1 | | 9/2003 | Johansson et al. |

FOREIGN PATENT DOCUMENTS

| DE | 44 17 476 | 11/1995 |
| DE | 195 30 220 | 2/1997 |
| DE | 195 47 986 | 7/1997 |
| WO | WO 94/27572 | 12/1994 |
| WO | WO 01/45649 | 6/2001 |
| WO | WO 01/90286 | 11/2001 |
| WO | WO 02/056843 | * 7/2002 ............... A61K 7/00 |

OTHER PUBLICATIONS

Search Report for PCT/BR2004/000160 dated Mar. 12, 2004.

* cited by examiner

*Primary Examiner* — Daniel Sullivan
*Assistant Examiner* — Barbara Frazier
(74) *Attorney, Agent, or Firm* — Alston & Bird LLP

(57) ABSTRACT

The present invention relates to a cosmetic microemulsion comprising a non-ionic surfactant type emulsifying agent, a co-emulsifying agent and a solvent selected from the group consisting of hexadecane and isomers thereof and dodecane and isomers thereof, said cosmetic microemulsions having particle diameter smaller than 100 nm. Preferably, this cosmetic microemulsion is used in the form of a pre-shampoo and has particles with a diameter on the order of 40 nm.

14 Claims, 2 Drawing Sheets

COSMETIC MICROEMULSION

This is a national stage application of PCT/BR2004/000160, filed Aug. 27, 2004, which is incorporated herein by reference in its entirety, and also claims priority of Brazilian patent application No. PI303286-8, filed Aug. 29, 2003, the disclosure thereof being hereby incorporated by reference.

The present invention relates to a cosmetic microemulsion comprising an emulsifying agent, which is a non-ionic surfactant, a co-emulsifying agent, solvent and water, being characterized as microemulsion by having a particle size on the order of 40 nm. These compositions are preferably pre-shampoos, that is to say, they are used before the usual hair washing and acting on the removing of residues found on the hair and on the scalp.

DESCRIPTION OF THE PRIOR ART

Today, several kinds of shampoos are available on the market, each one of these being composed of a specific combination of ingredients, thus providing different products for varied types of hair (shampoo for dry hair, for oily hair, for curly hair, for dyed hair, among others). In this regard, the result of hair cleaning becomes satisfactory. This specificity present in the formulation of each type of shampoo meets the needs of the consumer, until a gradual reduction in effectiveness of the cleaning provided by such products is noticed. With the passage of time, the hair of the user of shampoo begins to have an opaque or even dirty aspect due to the retention of residues and impurities.

In order to solve this problem, there are the anti-residue shampoos, which act to remove the shampoo residues left on the hair and scalp. The drawback noticed in using this shampoo is due to the anionic surfactant in its formulation. This component causes the opening of the scales of hair, which entails an opaque aspect of the hair. Although the hair is cleaner, it has an appearance of being badly treated.

The use of non-ionic surfactants was considered as a solution of this problem.

Document U.S. Pat. No. 5,885,563 discloses a shaving liquid composition composed of water, additives, a solvent being a hydrocarbon, preferably isohexadecane and a surfactant being n-decyl glycoside. However, this is an ordinary emulsion with large-diameter particles. This fact is harmful for cleaning, since this make it difficult to solubilize the dirt and also has a high interface tension between the water phase and the oil phase.

Document U.S. Pat. No. 6,555,119 discloses a transparent microemulsion, preferably used for skin care and comprising at least 2 non-ionic surfactants, at least 2 oily components, a water-soluble polymer and a cosmetically acceptable carrier. The particles of this microemulsion have diameters of about 100 nm, being preferably 80 nm. The function of the polymer in this composition is to eliminate stickiness inherent therein. This is a complex composition, that is to say, it is composed of considerable number of components and has particles with a relatively large diameter. These factors may by understood as higher manufacture cost due to the amount of components and lower cleaning power, since it comprises particles with relatively large diameters. Further, this document does not disclose how this composition acts to clean the skin.

OBJECTIVES OF THE INVENTION

The present invention has the objective of providing a cosmetic microemulsion that comprises an emulsifying agent that is a non-ionic surfactant, a co-emulsifying agent and a solvent that is preferably isohexadecane or dodecane or isomers thereof.

The function of this cosmetic microemulsion is to clean the hair by actuating on the removal of shampoo residues retained on it and on the scalp, being used as a pre-shampoo, that is, before applying the usual shampoo, without causing the scales of the hair to open, which would damage the cuticle. The cosmetic microemulsion of the present invention acts on the removal of residues of "leave-on" products, shampoos and conditioners.

SUMMARY OF THE INVENTION

The objective of the invention is to provide a cosmetic microemulsion that comprises an emulsifying agent of the non-ionic surfactant type, a co-emulsifying agent and a solvent selected from the group consisting of hexadecane and isomers thereof and dodecane and isomers thereof, said cosmetic microemulsion having particles with diameter smaller than 100 nm, preferably of about 40 nm.

BRIEF DESCRIPTION OF THE FIGURES

The present invention will now be described in greater detail with reference to the figures that illustrate the performance tests of the present invention.

DETAILED DESCRIPTION OF THE INVENTION

Figure 1:
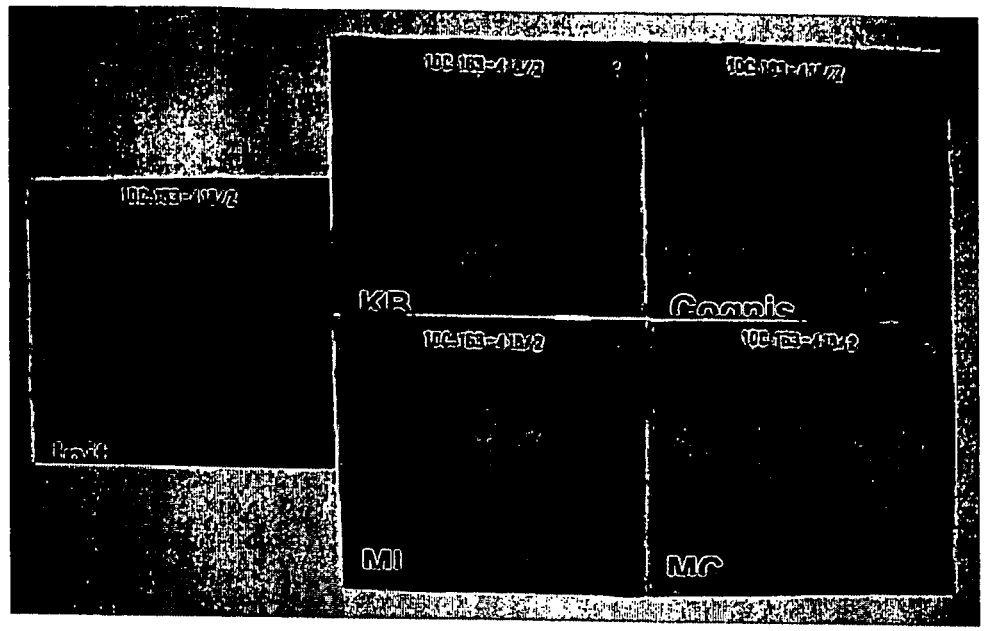
FIG. 1 illustrates the result of the colorimetry test by means of photos of samples, comparing the performance of the products of the prior art with the composition of the present invention.

The present invention discloses a cosmetic microemulsion, preferably in the form of a pre-shampoo, which comprises an emulsifying agent that is a non-ionic surfactant, a co-emulsifying agent and a solvent selected from the group consisting of hexadecane and isomers thereof and dodecane and isomers thereof, in addition to optional components that are added to this composition to provide determined desired characteristics. It is called a microemulsion because it is composed of particles having a diameter on the order of 100 nm, preferably on the order of 40 nm.

This composition acts on cleaning hair of shampoo users, being preferably used before washing said hair. The present invention has various advantages over known compositions, particularly shampoos, some of which are listed below:

the cosmetic microemulsion of the present invention acts on removing residues of "leave-on" products, shampoos and conditioners;
  this invention has a high cleaning power due to the solubilization/emulsification/penetration assembly, being capable of removing any kind of dirt present on one's hair;

alkyl polyglycoside, used in the present invention as an emulsifying agent, has a detergent property, which brings about greater effectiveness in cleaning hair of ordinary shampoo users;

the solvents used in the present cosmetic microemulsion help to solubilize dirt found on the hair and scalp in an effective way;

this cosmetic microemulsion acts to eliminate the "build-up" effect, that is to say, to eliminate the accumulation of residues inherent in shampoos;

these cosmetic microemulsions clean the hair and scalp much more effectively than the shampoos of the prior art, due to the extremely low interface tension between the water and oil phases, inherent in microemulsions;

due to the presence of a non-ionic surfactant, the hair scales do not open. The shampoos of the prior art comprise anionic surfactants which causes the open of the hair scales;

since the hair scales are not caused to open, the hair has an appearance of cleanliness and brightness and the hair cuticle do not suffer damages;

the cosmetic microemulsion of the present invention has various desirable properties in a cosmetic product, such as: low toxicity, low sensitizing, low irritation on one' skin and eyes, low activity of the surfactant on one's hair, it does not cause degradation of the hair;

alkyl polyglycoside is biodegradable, that it, using it does not cause damages to the environment.

These cosmetic microemulsions may further be used for preparing de make-up removers; face cleaning products, for example, face cleaning foam for oily, sensitive and/or acneic skin; degreasing lotion for oily hair or dandruffs; lotions for moistened handkerchiefs; shampoo formulas, among other cosmetic formulations.

Characteristics that define a microemulsion as well as the components that may be used in the present invention will now be described in greater detail.

Cosmetic Microemulsions

The microemulsions described herein are systems that comprise a mixture of oil (solvent), water, at least one emulsifying agent that is a non-ionic surfactant and a co-emulsifying agent, forming transparent or translucent, thermally stable, homogeneous emulsions with a particle size smaller than 100 nm.

Cosmetic applications of microemulsions include solubilizing fragrance in water, conditioning ordinary shampoo users' hair and cleaning the skin and hair. The solubilizing and cleaning power of the microemulsions is due to the extremely low interface tension between the water and oil phases.

Emulsifying Agent

In the cosmetic microemulsions of the present invention, only non-ionic surfactants are used. By preference, alkyl polyglycoside is used as a non-ionic surfactant, since the microemulsions containing this emulsifying agent are much sensitive to temperature than those that comprise other non-ionic surfactants. However, other non-ionic surfactants that are usually added to cosmetic compositions, more specifically to shampoo compositions may be used.

Alkyl polyglycosides are non-ionic surfactants sintered from renewable natural materials (fatty acids and saccharides). They are derived from ordinary natural organic monomeric units found in starch, fatty components and sugars, being preferably derived from D-glucose monomeric units. This type of emulsifying agent is of great interest, because it has favorable dermatologic properties, low toxicity and biodegradability. The surface activity of alkyl polyglycosides and their formation of micelles in diluted aqueous solutions are similar to those of ethoxylated fatty alcohols. Alkyl polyglycosides form microemulsions with low sensitivity to temperature, and the temperature is a crucial point for the phase inversion (a preferred process for preparing the present cosmetic composition described later) of the microemulsions formed by fatty and ethoxylated alcohols.

Alkyl glycosides may also be used as emulsifying agents.

Alkyl glycosides and alkyl polyglycosides may be defined as products from the condensation of long-chain alcohols such as $C_8$-$C_{30}$ alcohols with components that contain glucose like sugars or starches or else sugar and starch biopolymers. The preferred alcohols for this reaction are decyl alcohol, cetyl alcohol, stearyl alcohol, lauryl alcohol, oleyl alcohol, among others.

The preferred examples of alkyl polyglycoside used n the present invention as emulsifying agent are decyl polyglycoside and lauryl polyglycoside and isomers thereof and mixtures thereof. Also, preferred examples of alkyl glycoside for use in the present invention are: methyl glycoside, coco glycoside, lauryl glycoside, decyl glycoside and isomers thereof and mixtures thereof.

Preferably, decyl glycoside or an isomer thereof is used. This non-ionic surfactant is extremely soft and very stable. In this regard, it is recommendable for compositions applied to skin, including sensitive skins, face products, shower gel or liquid soap for the body and lotions for the body.

In the preferred embodiment, decyl glycoside or else more specifically Plantaren 2000®, produced by Cognis, is used as an emulsifying agent in an amount ranging from about 5% to about 20%, preferably from about 5% to about 12% and still more preferably from about 5% to about 8% by weight.

Co-Emulsifying Agent

The preferred co-emulsifying agent for the present invention is alkyl gluco glyceryl. This component helps in forming the microemulsions.

Alkyl gluco glyceryl is composed by an alkyl polyglycoside or an alkyl glycoside and a fatty acid monoglyceride. The alkyl polyglycoside or an alkyl glycoside used in the composition of alkyl gluco glyceryl may be any one of the components presented before as an emulsifying agent. The preferred ones are: decyl polyglycoside, lauryl polyglycoside, methyl glycoside, coco glycoside, lauryl glycoside, decyl glycoside and isomers thereof and mixtures thereof.

Examples of fatty acid glycerides that may be used for composing the alkyl gluco glyceryl are: glyceryl stearate, glyceryl monostearate, glyceryl isostearate, triglyceryl diisostearate, glyceryl miristate, glyceryl laurate, polyglyceryl-2 polyhydroxystearate, polyglyceryl-3 diisostearate, polyglyceryl-2 PEG-4 stearate, glyceryl oleate, glyceryl monooleate, PETG-10 glyceryl stearate, PEG-20 glyceryl stearate, PEG-80 glyceryl cocoate, PEG-8-glyceryl tallowate, PEG-200 glyceryl tallowate, glyceryl polymetacrylate, capric diglyceryl succinate, glyceryl tribehenate, glyceryl lanolate, polyglyceryl-3 oleate, polyglyceryl-4 isostearate, polyglycery-2 dipolyhydroxystearate, polyglyceryl-4 dipolyhydroxystearate, diistearaoylpolyglyceryl-3 diisostearate, polyglyceryl-2 dipolyhydroxystearate, polyglyceryl-3 dipolyhydroxystearate, polyglyceryl-2 laurate, isostearyl diglyceryl succinate, glyceryl stearate citrate, polyglyceryl methylglucose distearate, polyglyceryl-2 sesquiisostearate, α-octadecyl glyceryl ether, α-9-octadecenyl glyceryl ether, α-hexadecyl glyceryl ether, glyceryl monopalmitate, glyceride esters, diglyceride esters, among others.

In the initial embodiments, a combination of coco glycoside and glyceryl oleate, more specifically Lamesoft® PO 65, produced by Cognis, is used as a co-emulsifying agent in an amount ranging from about 3% to about 15%, preferably from about 3% to about 8%, and more preferably from about 3% to about 5% by weight.

Solvents

In the cosmetic microemulsions of the present invention, hexadecane, dodecane or isomers thereof, either combined or not are used. These solvents act on solubilizing the impurities and dirt found on the hair and scalp, providing a more effective cleaning.

Hexadecane has the molecular formula $C_{16}H_{34}$ and the following structural formula:

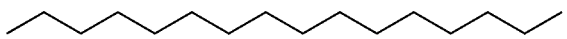 [SMILES: CCCCCCCCCCCCCCCC]

Hexadecane is also known as cetane, n-cetane and n-hexadecane. It has various isomers, among which 2-methylpentadecane and isohexadecane or 2,2,4,4,6,8,8-heptamethylnonane (HMN). The latter is the preferred one for use in the present composition.

Isohexadecane has the following structural formula.

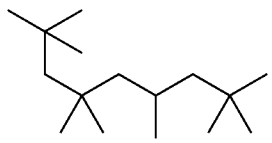 [SMILES: CC(CC(C)(C)C)CC(C)(C)CC(C)(C)C]

Isohexadecane is a mixture of isoparaffins $C_{16}$ with smaller proportions of $C_{12}$ and $C_{20}$ isoparaffins. The main component is 2,2,4,4,6,8,8-heptamethylnonane ($C_{16}H_{34}$). It is suitable for compositions that need exhibit pureness and absence of polar compounds. It has low toxicity, in addition to very low skin-irritation properties and is odorless and colorless.

Other solvent that may be used in the cosmetic compositions of the present invention is dodecane. This compound has the molecular formula $C_{12}H_{26}$ and the structural formula:

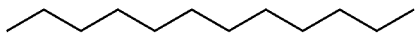

Dodecane is also known as adecane 12, alcane C(12), bihexyl, duodecane and n-dodecane. It has various isomers, among them 2,2,7,7 tetramethyloctane, 3,4-diethyl-3,4-dimetoxyhexane, 2,6-dimetnyldecane, 2,5-dimethyldecane and isododecane or 2,2-4,6,6-pentamethylheptane. The latter is the preferred one in this group for use in the present composition.

Isododecane has the following structural formula:

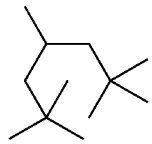

Isohexadecane is a mixture of $C_{12}$ isoparaffins, mainly consisting of 2,2,4,6,6-pentamethylheptane. This compound is specially indicated for applications that need to exhibit pureness and absence of polar compounds. It has very low toxicity, low color intensity, rapid evaporation, low skin-irritation property, besides being colorless.

In the preferred embodiments, hexadecane or preferably isohexadecane are used as solvent in an amount ranging from about 1% to about 8%, preferably from about 1% to about 5%, and more preferably from about 1% to bout 3% by weight.

Carrier—Water

By preference, water is used as a carrier of the compositions of the present invention. Such compositions comprise the adequate percentage for a sufficient amount (q.s.p.) so as to reach 100% of the formulation, based on its total weight. However, one may use other cosmetically acceptable carriers, usually added to cosmetic compositions of the prior art.

Optional Components

Moistening Agents

The moistening agent promotes water retention on the hair surface, since it supplies water to the hair and further prevents water loss thereof.

A few examples of moistening agents that may be added to the cosmetic microemulsions of the present invention are: lanolin oil, vaseline, glycols, polyalkylene glycols, alkylene polyols, monoethylene glycol, diethylene glycol, triethylene glycol, polyethylene glycol, propylene glycol, dipropylene glycol, polypropylene glycol, butylenes glycol, 1,3-butylene glycol, hexylene glycol, isoprene glycol, 1,2,6-hexanetriol, glycerol, ethoxylated glycerol, propoxylated glycerol, sorbitol, hydroxypropyl sorbitol, trietanolamine, alkoxylated glucose, hyaluronic acid, glycolic acid, lactic acid, glycolic acid, salicylic acid, clycerin, natural oils and mixture thereof.

In the preferred embodiments, propylene glycol or a combination of propylene glycol and trietanolamin are used as moistening agents in an amount ranging from about 1% to about 10%, preferably from about 1% to about 5%, and more preferably from about 1% to about 3% by weight.

Fragrance

Optionally, a perfume or fragrance selected from a variety of possible substances may be added. By preference, the fragrance Pretty® produced by Firmenich is used. The amount of fragrance to be added to the cosmetic compositions of the present invention preferably ranges from about 0.1% to about 1.0%, preferably from about 0.1% to about 0.5%, and more preferably from bout 0.1% to about 0.2% by weight.

Other Optional Components

In order to impart to the cosmetic microemulsions of the present invention some characteristic still not achieved by adding the components describes before, optional components that have physical and chemical compatibility with them may be added. A few of these compounds that may be added to the composition are:

a preservative: 2-bromo-2-nitro-1,3-propanodiol, methyl paraben, propyl paraben, imidazolidinyl urea, phenoxyetanol, DMDM hydantoin, quaternium-15;
    viscosity modifiers: sodium chloride and coco monoetanol amide;
    viscosity donating agents: natural and synthetic polymers, preferably Carbopol ETD 2020;
    antioxidant agents;
    antibacterial or antimicrobial agents;
    stylization agents;
    pearlizing agents: ethylene glycol disterate;
    opacifying agents: titanium dioxide;
    dyestuffs;
    vitamins;
    pH-adjusting agents: sodium hydroxide, calcium carbonate, citric acid, phosphoric acid.

The optional components cited above are the most commonly used in cosmetic compositions. However, there are other components that may be added to the cosmetic compositions of the present invention according to the intended purpose.

Preparation of the Cosmetic Microemulsions

Usually, the preparation of the microemulsions does not require mechanical energy, since they comprise high concentrations of emulsifying agents.

However, two methods are preferred for preparing the cosmetic microemulsions of the present invention, namely: 1) the process of homogenization under high pressure, which is recognizably used for preparing transparent products like the microemulsions, and 2) Phase Inversion Temperature (PIT) method, which provides transparent products with low contents of emulsifying agent. These two methods reduce the concentration of emulsifying agent necessary for obtaining the microemulsion.

The formulation of an oil-in-water type transparent microemulsion, instead of obtaining a bluish white oil-in-water type emulsion, as usual, is the result of the right choice of the components and of the preparation process. It is known that the particle size of the microemulsion depends upon the curvature which the emulsifying agent can establish in the polar/non-polar interface.

The reduction of the interface tension, achieving ultralow numbers depends upon the adsorption of the emulsifying/co-emulsifying agents on the surface of the oil droplet. The balance between the oil-in-water emulsifying agent and the balance between the water-in-oil emulsifying agent in the phase inversion process are necessary for the formulation of the microemulsion. The choice of the oil phase is another critical factor that determines the formation of a transparent product.

In order to obtain the formation of the microemulsion, one should follow these steps (while cooling the mixture):
1. formation of the water-in-oil emulsion;
2. inversion phase, and
3. formation of the oil-in-water microemulsion.

Preparation Process

The process of preparing the cosmetic compositions of the present invention consists in heating the water phase and oil phase up to a temperature of 85° C., after slowly adding the water phase to the oil phase under stirring. After the mixing, one should cool the composition until a temperature of 30° C. is reached.

EXAMPLES

The following examples are preferred variations of the cosmetic compositions of the present invention and should not be interpreted as being limitations thereof. In this regard, it should be understood that the scope of the present invention embraces other possible variations, being limited only by the contents of the accompanying claims, which include the possible equivalents.

Example 1

| Components | Mass composition (%) |
|---|---|
| Plantaren 2000 ® (decyl glycoside) | 12.00 |
| Lamesoft ® PO 65 (alkyl gluco glyceryl M. Lipo) | 8.00 |
| Isohexadecane | 2.00 |
| water | 100 (q.s.p.) |
| trietanolamine | 0.50 |
| Propylene glycol | 2.00 |
| DMDM Hdantoin | 0.05 |
| Fragrance Pretty ® | 0.10 |

Example 2

| Components | Mass composition (%) |
|---|---|
| Plantaren 2000 ® (decyl glycoside) | 5.20 |
| Lamesoft ® PO 65 (alkyl gluco glyceryl M. Lipo) | 3.20 |
| Isododecane | 2.00 |
| Water | 100 (q.s.p.) |
| Propylene glycol | 2.00 |
| DMDM hydantoin | 0.05 |
| Fragrance Pretty ® | 0.20 |

Tests

We now present tests that were performed to evaluate the performance of the cosmetic compositions of the present invention. Pre-shampoos produced by Cognis (Cognis 19) and by Johnson & Johnson (KB2) were used:

1) Colorimetry

This test was carried out to evaluate the dirt removing power of formulations applied to a substrate. The substrate used is a standard fabric (10C.163418/2), impregnated with a mixture of fatty acids, lanolin and pigment. The equipment used is the Spectrophotometer GrematMacbeth Color-EYE 2180/2180UV. Twenty substrates were used in this test. The steps of the colorimetry test carried out were the following:
  initial reading were carried out on the substrate;
  0.5 ml of pre-shampoo (products equivalent to the present invention and the present invention) was applied to the substrates, which was maintained at rest for 2 minutes;
  each substrate was dipped into a beaker containing a standard (5%) shampoo solution;
  the solutions containing the substrate were stirred for 2 minutes;
  with the dry substrates, one effected the colorimetry measurement.

Result:

From the photos illustrated in FIG. 1 it can be noticed that the formula MI04 (cosmetic microemulsion of the present invention) exhibited better removal of dirt among the evaluated formulations. From an examination of FIG. 1, it follows that the white stain formed in the center of the substrate caused by the formula MI04 has greater contrast in color with respect to the color of the fabric, which confirms its higher effectiveness in cleaning and removing dirt.

Figure 2:
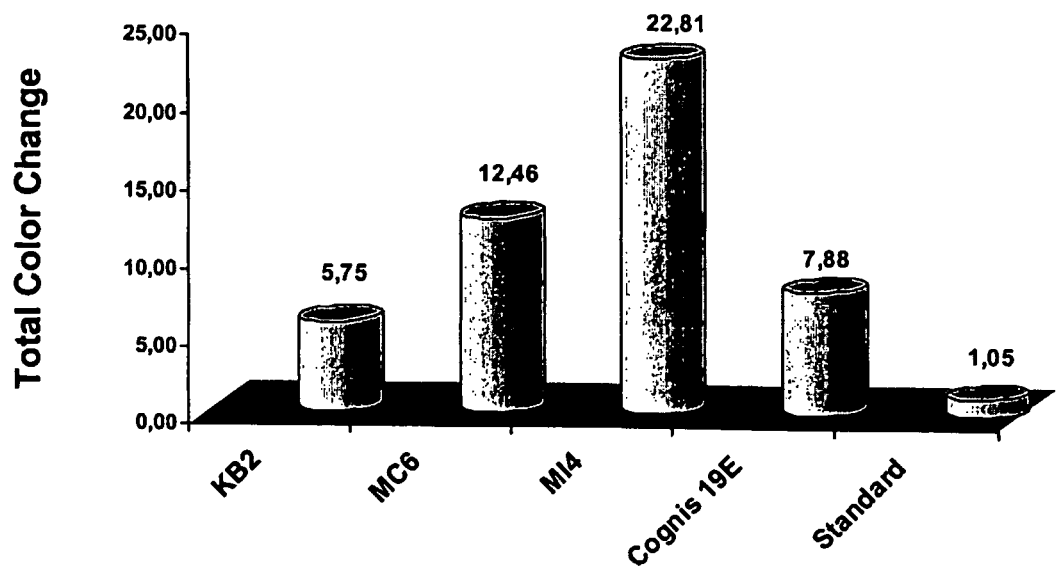
FIG. 2 is a graph representing numerically the result illustrated in FIG. 1.

Once more, according to the graph in FIG. 2, one can conclude that the microemulsion of the present invention (MI04) is superior to the other compositions.

2) Fluorescence

This test evaluates the power of removal of cationic polymers and silicones of formulations applied to ordinary shampoo users' hair. The hair was placed on glass blades and examined under a Leica fluorescence microscope. The fluorescence intensity was examined with the help of a cube N 2.1 barrier filter, the excitement region of which is 515-560 nm. The cationic fluorescent marker used is the Rhodamina B C1

Basic, which interacts with sulfonic groups produced by the oxidative treatments already present on the hair. The steps of the fluorescence test carried out were the following.

- the hair was treated with cationic polymers (guar gum and amodimeticone);
- the hair was washed with a mixture of pre-shampoo and a standard shampoo;
- then, the hair was exposed for 2 minutes in Rhodamina Bo solution;
- the fluorescence measurement was made.

Figure 3:
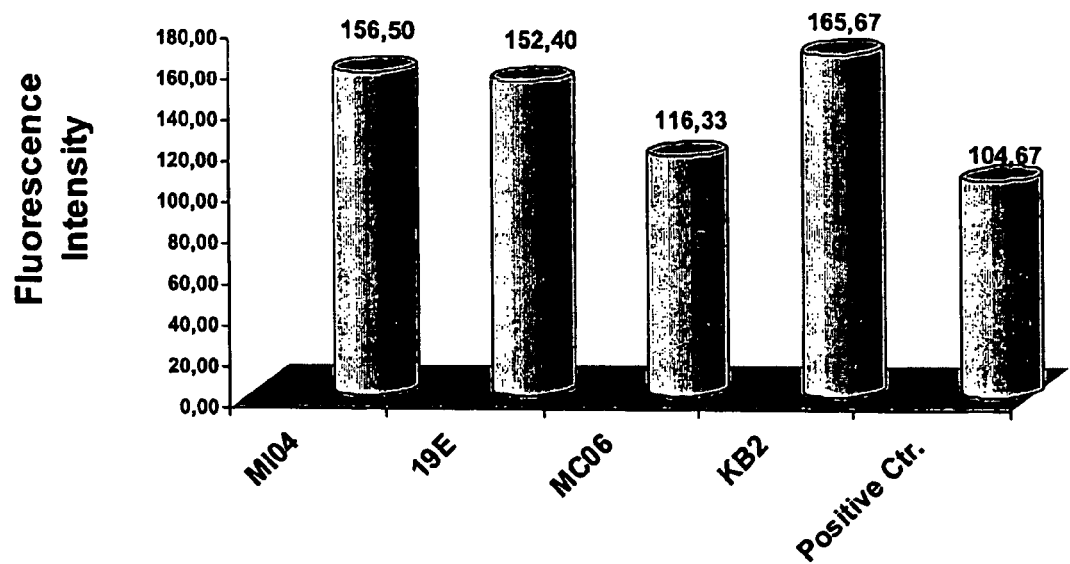
FIG. 3 is a graph representing numerically the result of the fluorescence test, comparing the performance of products of the prior art with the composition of the present invention.

Result:

From the graph in FIG. 3 it follows that the rate of removal of cationic polymers and of silicones is virtually equal for the formulas MI04, 19E and KB2. However, the formula KB2 contains anionic surfactant in its formulation, which causes the hair scales to open, damaging the hair cuticle.

3) Electronic Scanning Microscopy Coupled with EDS

The electronic scanning microscopy (ESM), together with the use of Electronic Microprobe (EM/EDS) enables one to evaluate the morphology, texture, distribution of the chemical elements that compose the hair fiber, as well as determine the possible transformations of the microstructure during the treatment of this fiber.

In order to characterize the deposition of silicon on the hair fiber, samples were cut with scissors and secured to sample holders made of copper by using a double-face carbon conductive tape, specially designed for electronic scanning microscopy.

The samples were then positioned in the low-vacuum chamber and then the work distance conditions were adjusted at 27 mm, acceleration voltage at 20 kV, focus and "Spoot Size". These conditions were maintained constant for all the evaluations.

The results of the EDS spectra have their intensity expressed in counts per second, on the ordinate axis, and the corresponding energies in keV, on the abscissas axis (graph not shown). The position of the energy line is characteristic for each chemical element, and the intensity is proportional to the amount of the element present in the sample.

In order to help the viewing of the arrangement of the silicon element, the mapping of this element on the hair fiber was performed, resulting in the attached graph.

Figure 4:
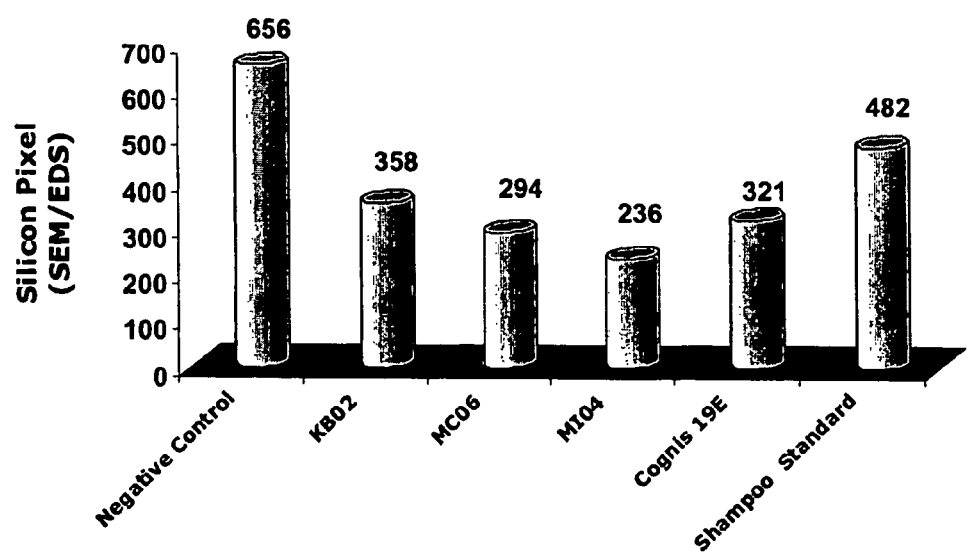
FIG. 4 is a graph representing numerically the result of electronic scanning microscopy test coupled with EDS, comparing the performance of products of the prior art with the composition of the present invention.

Result:

From the electronic scanning test with EDS illustrated on FIG. 4 it can be noted that the formula MI04 is the best one in removing silicone, since the substrate underlying it has lower concentration of this component.

4) GAP Test

This test was carried out on 138 people, 68 of whom tested the formula MI04, and the remaining 70 tested the formula MC06. These people used ordinary shampoo, conditioner and a leave-on product for 7 days. After this period, they used a single time the formulas MI04 and MC06 as follows: they applied them to the still wet hair, leaving them to act for 2 minutes. After this interval, they applied standard shampoo over the formula, massaging the whole hair, removing the shampoo, applying the conditioner and then removing it.

As a result, no differences were noticed between the use of the formulas MI04 and MC06 which were considered regular.

Now, using the hair-type criterion for the formation of the groups, the groups composed of mixed or dry hair indicated more preference for the formula MI04 than the groups composed of oily and normal hair.

The following positive points were considered: perceptible hair cleaning, loose hair effect and increase in hair volume.

The invention claimed is:

1. A cosmetic microemulsion for removing of residues of leave-on products, shampoos and conditioners consisting essentially of:
    5% to 20%, by weight, of a non-ionic-surfactant emulsifying agent; said non-ionic-surfactant emulsifying agent is an alkyl polyglycoside,
    from 3% to 15%, by weight, of a co-emulsifying agent; said co-emulsifying agent is an alkyl gluco glyceryl; and
    from 1% to 8%, by weight, of a solvent selected from the group consisting of hexadecane and isomers thereof and dodecane and isomers thereof, wherein said cosmetic microemulsion has particle diameters smaller than 100 nm.

2. A cosmetic microemulsion according to claim 1, wherein the particles have diameters of about 40 nm.

3. A cosmetic microemulsion according to claim 1, wherein the amount of emulsifying agent ranges from 5% to 12% by weight.

4. A cosmetic microemulsion according to claim 3, wherein the amount of emulsifying agent ranges from 5% to 8% by weight.

5. A cosmetic microemulsion according to claim 1, wherein the co-emulsifying agent is an alkyl gluco glyceryl composed of an alkyl polyglycoside or an alkyl glycoside and a fatty acid monoglyceride.

6. A cosmetic microemulsion according to claim 1, wherein the amount of co-emulsifying agent ranges from 3% to 8% by weight.

7. A cosmetic microemulsion according to claim 6, wherein the amount of co-emulsifying agent ranges from 3% to 5% by weight.

8. A cosmetic microemulsion according to claim 1, wherein the solvent is hexadecane or an isomer thereof.

9. A cosmetic microemulsion according to claim 8, wherein the solvent is isohexadecane.

10. A cosmetic microemulsion according to claim 1, wherein the solvent is dodecane or an isomer thereof.

11. A cosmetic microemulsion according to claim 1, wherein the solvent is isododecane.

12. A cosmetic microemulsion according to claim 1, wherein the amount of solvent ranges from 1% to 5% by weight.

13. A cosmetic microemulsion according to claim 12, wherein the amount of solvent ranges from 1% to 3% by weight.

14. A cosmetic microemulsion for removing of residues of leave-on products, shampoos and conditioners consisting essentially of:
    5% to 20%, by weight, of a non-ionic-surfactant emulsifying agent; said non-ionic-surfactant emulsifying agent is an alkyl polyglycoside,
    from 3% to 15%, by weight, of a co-emulsifying agent; said co-emulsifying agent is a combination of (i) coco glycoside and (ii) glyceryl oleate; and
    from 1% to 8%, by weight, of a solvent selected from the group consisting of hexadecane and isomers thereof and dodecane and isomers thereof, wherein said cosmetic microemulsion has particle diameters smaller than 100 nm.

* * * * *

UNITED STATES PATENT AND TRADEMARK OFFICE
CERTIFICATE OF CORRECTION

PATENT NO. : 8,715,631 B2  Page 1 of 1
APPLICATION NO. : 10/569433
DATED : May 6, 2014
INVENTOR(S) : Araujo et al.

It is certified that error appears in the above-identified patent and that said Letters Patent is hereby corrected as shown below:

On the Title Page item (73),
Delete "Natura Cosmetics S.A.,:" and insert --Natura Cosmeticos S.A.-- therefor.

Signed and Sealed this
Nineteenth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,715,631 B2                                          Page 1 of 1
APPLICATION NO.  : 10/569433
DATED            : May 6, 2014
INVENTOR(S)      : Araujo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1180 days.

Signed and Sealed this

Twenty-ninth Day of September, 2015

Michelle K. Lee
*Director of the United States Patent and Trademark Office*